US00PP16805P2

(12) United States Plant Patent
Iwaki et al.

(10) Patent No.: US PP16,805 P2
(45) Date of Patent: Jul. 11, 2006

(54) ***PETUNIA* PLANT NAMED 'SUNSURFBUPA'**

(50) Latin Name: *Petunia×hybrida*
Varietal Denomination: Sunsurfbupa

(75) Inventors: Kazunari Iwaki, Shiga (JP); Takuro Ishihara, Tokyo (JP); Shinya Miyano, Tounosyou-machi (JP)

(73) Assignees: Keisei Rose Nurseries Inc., Tokyo (JP); Suntory Flowers Ltd., Tokyo (JP)

( * ) Notice: Subject to any disclaimer, the term of this patent is extended or adjusted under 35 U.S.C. 154(b) by 38 days.

(21) Appl. No.: 11/091,809

(22) Filed: Mar. 28, 2005

(51) Int. Cl.
*A01H 5/00* (2006.01)

(52) U.S. Cl. ..... Plt./356
(58) Field of Classification Search ..... Plt./356
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Petunia* plant named 'Sunsurfbupa', characterized by its outwardly spreading, mounded and decumbent plant habit; vigorous and freely branching growth habit; freely flowering habit; purple-colored flowers; long flowering period; and good garden performance.

1 Drawing Sheet

Botanical designation: *Petunia×hybrida.*
Cultivar denomination: 'Sunsurfbupa'.

BACKGROUND OF THE INVENTION

The present Invention relates to a new and distinct cultivar of *Petunia* plant, botanically known as *Petunia×hybrida,* and hereinafter referred to by the cultivar name Sunsurfbupa.

The new *Petunia* is a product of a planned breeding program conducted by the Inventors in Higashiomi, Shiga, Japan. The objective of the breeding program is to create new *Petunias* with numerous flowers with attractive flower colors.

The new *Petunia* originated from a cross-pollination made by the Inventors in August, 2001, of the *Petunia* cultivar Super Cascade Blue, not patented, as the female, or seed, parent with a proprietary *Petunia* selection identified as code 79-200, not patented, as the male, or pollen, parent. The new *Petunia* was selected as a single plant from the resulting progeny of the cross-pollination by the Inventors in a controlled environment in Higashiomi, Shiga, Japan.

Asexual reproduction of the new cultivar by terminal cuttings in a controlled environment in Higashiomi, Shiga, Japan since September, 2003 has shown that the unique features of this new *Petunia* are stable and reproduced true to type in successive generations.

SUMMARY OF THE INVENTION

Plants of the cultivar Sunsurfbupa have not been observed under all possible environmental conditions. The phenotype may vary somewhat with variations in environment such as temperature and light intensity without, however, any variance in genotype.

The following traits have been repeatedly observed and are determined to be the unique characteristics of 'Sunsurfbupa'. These characteristics in combination distinguish 'Sunsurfbupa' as a new and distinct *Petunia* cultivar:

1. Outwardly spreading, mounded and decumbent plant habit.

2. Vigorous and freely branching growth habit.
3. Freely flowering habit.
4. Purple-colored flowers.
5. Long flowering period.
6. Good garden performance.

Plants of the new *Petunia* differ from plants of the female parent, the cultivar Super Cascade Blue, in the following characteristics:

1. Plants of the new *Petunia* are shorter and broader than plants of the cultivar Super Cascade Blue.
2. Plants of the new *Petunia* flower for a longer period of time than plants of the cultivar Super Cascade Blue.

Plants of the new *Petunia* differ from plants of the male parent selection in the following characteristics:

1. Plants of the new *Petunia* are taller and broader than plants of the male parent selection.
2. Plants of the new *Petunia* have larger flowers than plants of the male parent selection.

Plants of the new *Petunia* can be compared to plants of the cultivar Revolution Violet No. 3, disclosed in U.S. Plant Pat. No. 10,330. In side-by-side comparisons conducted in Higashiomi, Shiga, Japan, plants of the new *Petunia* differed from plants of the cultivar Revolution Violet No. 3 in the following characteristics:

1. Plants of the new *Petunia* were shorter than plants of the cultivar Revolution Violet No. 3.
2. Plants of the new *Petunia* had narrower lateral branches than plants of the cultivar Revolution Violet No. 3.
3. Plants of the new *Petunia* had longer, but narrower, leaves than plants of the cultivar Revolution Violet No. 3.
4. Plants of the new *Petunia* and the cultivar Revolution Violet No. 3 differed in petal coloration as plants of the cultivar Revolution Violet No. 3 had purple violet-colored petals.
5. Plants of the new *Petunia* and the cultivar Revolution Violet No. 3 differed in flower throat and tube coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia*.

The photograph at the top of the sheet comprises a side perspective view of a typical flowering plant of 'Sunsurfbupa' grown in a container.

The photograph at the bottom of the sheet comprises a close-up view of typical flowers and leaves of 'Sunsurfbupa'.

DETAILED BOTANICAL DESCRIPTION

The aforementioned photographs and following observations and measurements describe plants grown in Higashiomi, Shiga, Japan, in 15-cm containers for about four months in an outdoor nursery during the spring and early summer with day temperatures about 23° C. and night temperatures about 15° C. Plants were pinched one time in the early spring. Color references are made to The Royal Horticultural Society Colour Chart, 2001 Edition, except where general terms of ordinary dictionary significance are used.

Botanical classification: *Petunia×hybrida* cultivar Sunsurfbupa.

Parentage:

*Female, or seed, parent.*—*Petunia×hybrida* cultivar Super Cascade Blue, not patented.

*Male, or pollen, parent.*—Proprietary *Petunia×hybrida* selection identified as code 79-200, not patented.

Propagation:

*Type cutting.*—Terminal vegetative cuttings.

*Time to initiate roots.*—About one week at 20 to 25° C.

*Time to develop roots.*—About three weeks at 20 to 25° C.

*Root description.*—Fine, fibrous, fleshy; light brown in color.

*Rooting habit.*—Freely branching.

Plant description:

*Plant and growth habit.*—Annual flowering plant; indeterminate; outwardly spreading, mounded and decumbent plant habit. Viscid and glandular pubescent. Vigorous growth habit. Freely branching habit with lateral branches developing potentially at every node.

*Plant height.*—About 13.8 cm.

*Plant diameter.*—About 50 cm.

*Lateral branches.*—Length: About 25.6 cm. Diameter: About 2.6 mm. Internode length: About 1 cm. Texture: Pubescent. Color: 144A.

*Foliage description.*—Arrangement: Alternate, simple; sessile. Length: About 5.5 cm. Width: About 2.9 cm. Shape: Ovate. Apex: Obtuse. Base: Cuneate. Margin: Entire. Texture, upper and lower surfaces: Pubescent; viscid. Venation pattern: Pinnate; reticulate. Color: Developing and fully expanded foliage, upper surface: 137A. Developing and fully expanded foliage, lower surface: 137C. Venation, upper and lower surfaces: Similar to lamina.

Flower description:

*Flower type and habit.*—Single salverform flowers; flowers face mostly upward or outward; axillary. Flowers not persistent. Freely flowering habit.

*Natural flowering season.*—Long flowering period, plants flower from spring through late autumn in Japan; flowering continuous during this period.

*Flower longevity on the plant.*—About five days.

*Fragrance.*—Faint.

*Flower size.*—Diameter: About 7.4 cm. Length: About 4.7 cm.

*Flower buds.*—Length: About 3.8 cm. Diameter: About 7 mm. Shape: Cylindrical. Color: N79B.

*Corolla.*—Quantity/arrangement: Five petals; fused, funnelform. Petal length: About 2.6 cm. Petal width: About 3 cm. Petal shape: Roughly spatulate to fan-shaped. Petal apex: Cuspidate. Petal margin: Entire; undulate. Petal texture, upper and lower surfaces: Smooth; satiny. Color: Petal, when developing and fully expanded, upper surface: N87A; venation, 83A. Petal, when developing and fully expanded, lower surface: N78C; venation, 83A. Flower throat (inside): 77B; venation, N79A. Flower tube (outside): 77B.

*Sepals.*—Arrangement/appearance: Single whorl of five sepals fused at base, star-shaped. Length: About 1.5 cm. Width: About 5 mm. Shape: Narrowly oblong. Apex: Obtuse. Margin: Entire. Texture, upper and lower surfaces: Pubescent. Color, immature, upper and lower surfaces: 137A. Color, mature, upper and lower surfaces: 137A.

*Peduncles.*—Length: About 2.3 cm. Width: About 1 mm. Strength: Moderately strong. Texture: Pubescent. Color: 144A.

*Reproductive organs.*—Stamens: Quantity: Five per flower. Anther shape: Ellipsoidal. Anther length: About 2 mm. Anther color: 91B. Pollen amount: Moderate. Pollen color: 94B. Pistils: Quantity: One per flower. Pistil length: About 2 cm. Style length: About 1.8 cm. Style color: 144C. Stigma shape: Broadly elliptic. Stigma color: 143A. Ovary color: 144B.

*Seeds.*—Seed development has not been observed.

Disease/pest resistance: Plants of the new *Petunia* have not been noted to be resistant to specific pathogens and pests common to *Petunia*.

Garden performance: Plants of the new *Petunia* have been observed to have good garden performance and tolerate rain, wind and tolerated temperatures from 5 to 35° C.

It is claimed:

1. A new and distinct cultivar of *Petunia* plant named 'Sunsurfbupa', as illustrated and described.

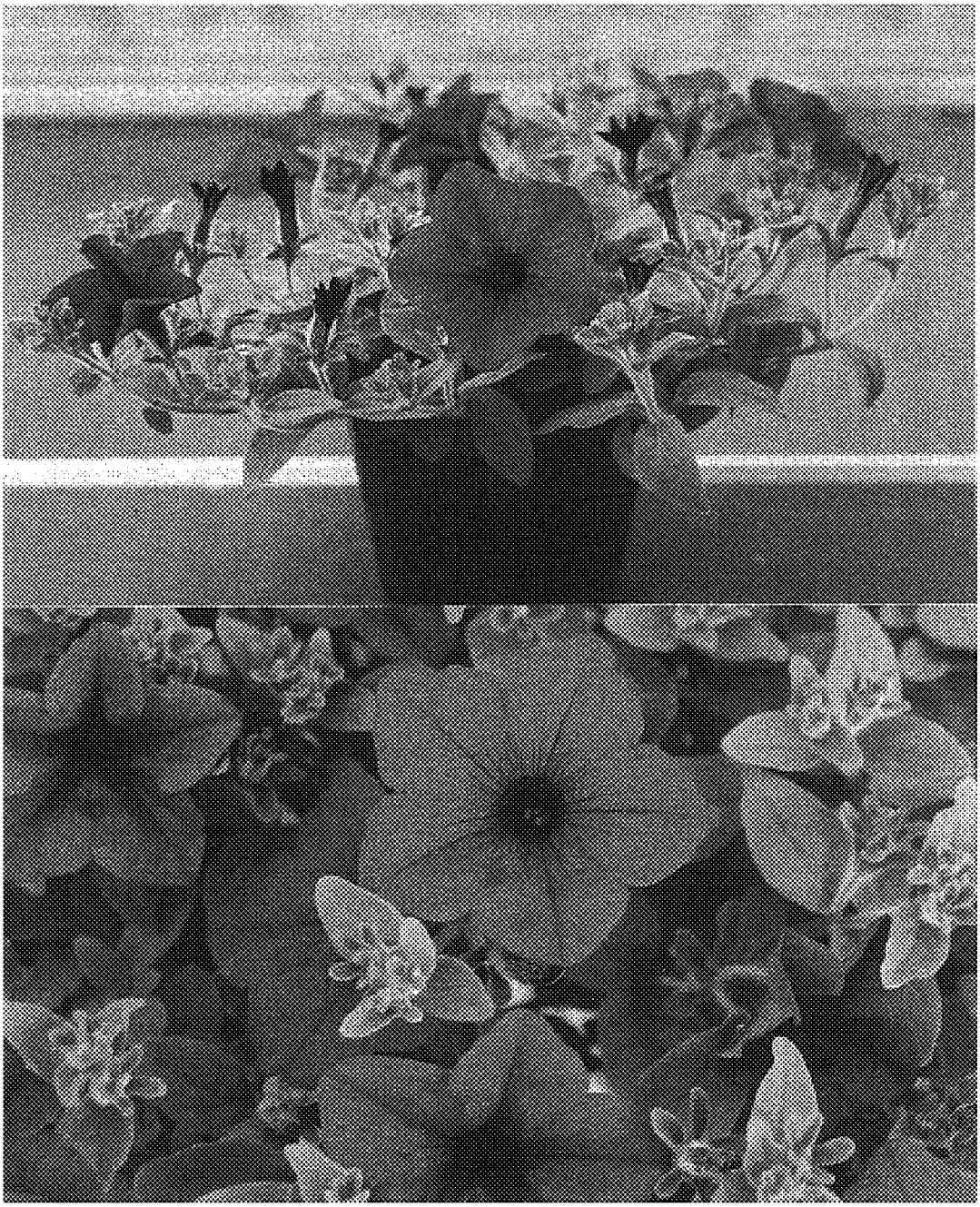

* * * * *